(12) United States Patent
Nakagami et al.

(10) Patent No.: US 9,872,825 B2
(45) Date of Patent: Jan. 23, 2018

(54) PEPTIDE WITH ANTI-AGING EFFECT AND USE THEREOF

(71) Applicant: OSAKA UNIVERSITY, Osaka (JP)

(72) Inventors: Hironori Nakagami, Osaka (JP); Ryuichi Morishita, Osaka (JP); Hideki Tomioka, Osaka (JP); Akiko Tenma, Osaka (JP)

(73) Assignee: Osaka University, Osaka (JP)

( * ) Notice: Subject to any disclaimer, the term of this patent is extended or adjusted under 35 U.S.C. 154(b) by 128 days.

(21) Appl. No.: 14/780,122

(22) PCT Filed: Mar. 27, 2014

(86) PCT No.: PCT/JP2014/058786
§ 371 (c)(1),
(2) Date: Dec. 22, 2015

(87) PCT Pub. No.: WO2014/157485
PCT Pub. Date: Oct. 2, 2014

(65) Prior Publication Data
US 2016/0101032 A1    Apr. 14, 2016

(30) Foreign Application Priority Data

Mar. 29, 2013 (JP) ................................ 2013-071791

(51) Int. Cl.
| | | |
|---|---|---|
| *A61K 8/64* | (2006.01) | |
| *A61Q 19/08* | (2006.01) | |
| *C07K 7/08* | (2006.01) | |
| *A61K 38/10* | (2006.01) | |
| *C07K 7/06* | (2006.01) | |
| *A23L 33/18* | (2016.01) | |

(52) U.S. Cl.
CPC ................ *A61K 8/64* (2013.01); *A23L 33/18* (2016.08); *A61K 38/10* (2013.01); *A61Q 19/08* (2013.01); *C07K 7/06* (2013.01); *C07K 7/08* (2013.01); *A61K 2800/78* (2013.01)

(58) Field of Classification Search
None
See application file for complete search history.

(56) References Cited

U.S. PATENT DOCUMENTS

| | | |
|---|---|---|
| 2007/0281888 A1 | 12/2007 | Nishikawa et al. |
| 2008/0032917 A1* | 2/2008 | Li ............................ C12Q 1/18 530/324 |
| 2012/0122766 A1 | 5/2012 | Gemba et al. |
| 2012/0172287 A1 | 7/2012 | Gemba et al. |
| 2014/0044655 A1 | 2/2014 | Dal Farra et al. |

FOREIGN PATENT DOCUMENTS

| | | |
|---|---|---|
| JP | 2011042613 A | 3/2011 |
| JP | 2013129648 A1 | 7/2013 |
| WO | WO-2005090564 A1 | 9/2005 |
| WO | WO-2008096814 A1 | 8/2008 |
| WO | WO-2010061915 A1 | 6/2010 |
| WO | WO-2010137594 A1 | 12/2010 |
| WO | WO-2012140331 A1 | 10/2012 |

OTHER PUBLICATIONS

Akiko Tenma et al., "Development of functional peptides with anti-aging effects and antimicrobial activity", Fragrance Journal, 2012, vol. 40, No. 6, pp. 59-63.
International Search Report and Written Opinion in corresponding PCT/JP2014/058786 dated Jun. 24, 2014.
International Preliminary Report on Patentability in corresponding PCT/JP2014/058786 dated Mar. 26, 2015.
Extended European Search Report in corresponding PCT/JP2014/058786, dated Jul. 25, 2016.

* cited by examiner

*Primary Examiner* — Karlheinz R. Skowronek
*Assistant Examiner* — Ronald T Niebauer
(74) *Attorney, Agent, or Firm* — Leydig, Voit & Mayer, Ltd.

(57) ABSTRACT

An object of the present invention to discover a short peptide having an anti-aging effect and to provide a novel anti-aging agent comprising the peptide as an active ingredient. The inventors have discovered that a peptide consisting of an amino acid sequence ELKLIFLHRLKRLRKRLKRK (SEQ ID NO: 1) or a partial sequence thereof and having one or more effects selected from the group consisting of promoting fibroblast growth, promoting hyaluronic acid production and contracting a collagen gel, or a derivative or salt of the peptide is useful as an active ingredient of an anti-aging agent.

23 Claims, 3 Drawing Sheets

JP13-254
Data: <Untitled>.G13 26 Nov 2013 13:50 Cal: 1000 16 Jul 2013 12:05
Kratos PC Axima CFR V2.3.5: Mode linear, Power: 95, P.Ext. @ 1000 (bin 62)
  %Int.    55 mV  Profiles 19-20:

SEQUENCE LISTING

```
<160> NUMBER OF SEQ ID NOS: 23

<210> SEQ ID NO 1
<211> LENGTH: 20
<212> TYPE: PRT
<213> ORGANISM: Artificial Sequence
<220> FEATURE:
<223> OTHER INFORMATION: synthesized peptide

<400> SEQUENCE: 1

Glu Leu Lys Leu Ile Phe Leu His Arg Leu Lys Arg Leu Arg Lys Arg
1               5                   10                  15

Leu Lys Arg Lys
```

-continued

```
                20

<210> SEQ ID NO 2
<211> LENGTH: 5
<212> TYPE: PRT
<213> ORGANISM: Artificial Sequence
<220> FEATURE:
<223> OTHER INFORMATION: synthesized peptide

<400> SEQUENCE: 2

Glu Leu Lys Leu Ile
1               5

<210> SEQ ID NO 3
<211> LENGTH: 5
<212> TYPE: PRT
<213> ORGANISM: Artificial Sequence
<220> FEATURE:
<223> OTHER INFORMATION: synthesized peptide

<400> SEQUENCE: 3

Leu Lys Leu Ile Phe
1               5

<210> SEQ ID NO 4
<211> LENGTH: 5
<212> TYPE: PRT
<213> ORGANISM: Artificial Sequence
<220> FEATURE:
<223> OTHER INFORMATION: synthesized peptide

<400> SEQUENCE: 4

Lys Leu Ile Phe Leu
1               5

<210> SEQ ID NO 5
<211> LENGTH: 5
<212> TYPE: PRT
<213> ORGANISM: Artificial Sequence
<220> FEATURE:
<223> OTHER INFORMATION: synthesized peptide

<400> SEQUENCE: 5

Leu Ile Phe Leu His
1               5

<210> SEQ ID NO 6
<211> LENGTH: 5
<212> TYPE: PRT
<213> ORGANISM: Artificial Sequence
<220> FEATURE:
<223> OTHER INFORMATION: synthesized peptide

<400> SEQUENCE: 6

Ile Phe Leu His Arg
1               5

<210> SEQ ID NO 7
<211> LENGTH: 5
<212> TYPE: PRT
<213> ORGANISM: Artificial Sequence
<220> FEATURE:
<223> OTHER INFORMATION: synthesized peptide

<400> SEQUENCE: 7

Phe Leu His Arg Leu
1               5
```

```
<210> SEQ ID NO 8
<211> LENGTH: 5
<212> TYPE: PRT
<213> ORGANISM: Artificial Sequence
<220> FEATURE:
<223> OTHER INFORMATION: synthesized peptide

<400> SEQUENCE: 8

Leu His Arg Leu Lys
1               5

<210> SEQ ID NO 9
<211> LENGTH: 5
<212> TYPE: PRT
<213> ORGANISM: Artificial Sequence
<220> FEATURE:
<223> OTHER INFORMATION: synthesized peptide

<400> SEQUENCE: 9

His Arg Leu Lys Arg
1               5

<210> SEQ ID NO 10
<211> LENGTH: 5
<212> TYPE: PRT
<213> ORGANISM: Artificial Sequence
<220> FEATURE:
<223> OTHER INFORMATION: synthesized peptide

<400> SEQUENCE: 10

Arg Leu Lys Arg Leu
1               5

<210> SEQ ID NO 11
<211> LENGTH: 5
<212> TYPE: PRT
<213> ORGANISM: Artificial Sequence
<220> FEATURE:
<223> OTHER INFORMATION: synthesized peptide

<400> SEQUENCE: 11

Leu Lys Arg Leu Arg
1               5

<210> SEQ ID NO 12
<211> LENGTH: 5
<212> TYPE: PRT
<213> ORGANISM: Artificial Sequence
<220> FEATURE:
<223> OTHER INFORMATION: synthesized peptide

<400> SEQUENCE: 12

Lys Arg Leu Arg Lys
1               5

<210> SEQ ID NO 13
<211> LENGTH: 5
<212> TYPE: PRT
<213> ORGANISM: Artificial Sequence
<220> FEATURE:
<223> OTHER INFORMATION: synthesized peptide

<400> SEQUENCE: 13

Arg Leu Arg Lys Arg
1               5
```

```
<210> SEQ ID NO 14
<211> LENGTH: 5
<212> TYPE: PRT
<213> ORGANISM: Artificial Sequence
<220> FEATURE:
<223> OTHER INFORMATION: synthesized peptide

<400> SEQUENCE: 14

Leu Arg Lys Arg Leu
1               5

<210> SEQ ID NO 15
<211> LENGTH: 5
<212> TYPE: PRT
<213> ORGANISM: Artificial Sequence
<220> FEATURE:
<223> OTHER INFORMATION: synthesized peptide

<400> SEQUENCE: 15

Arg Lys Arg Leu Lys
1               5

<210> SEQ ID NO 16
<211> LENGTH: 5
<212> TYPE: PRT
<213> ORGANISM: Artificial Sequence
<220> FEATURE:
<223> OTHER INFORMATION: synthesized peptide

<400> SEQUENCE: 16

Lys Arg Leu Lys Arg
1               5

<210> SEQ ID NO 17
<211> LENGTH: 5
<212> TYPE: PRT
<213> ORGANISM: Artificial Sequence
<220> FEATURE:
<223> OTHER INFORMATION: synthesized peptide

<400> SEQUENCE: 17

Arg Leu Lys Arg Lys
1               5

<210> SEQ ID NO 18
<211> LENGTH: 4
<212> TYPE: PRT
<213> ORGANISM: Artificial Sequence
<220> FEATURE:
<223> OTHER INFORMATION: synthesized peptide

<400> SEQUENCE: 18

Arg Leu Lys Arg
1

<210> SEQ ID NO 19
<211> LENGTH: 3
<212> TYPE: PRT
<213> ORGANISM: Artificial Sequence
<220> FEATURE:
<223> OTHER INFORMATION: synthesized peptide

<400> SEQUENCE: 19

Leu Lys Arg
1
```

```
<210> SEQ ID NO 20
<211> LENGTH: 16
<212> TYPE: PRT
<213> ORGANISM: Artificial Sequence
<220> FEATURE:
<223> OTHER INFORMATION: synthesized peptide

<400> SEQUENCE: 20

Lys Leu Ile Phe Leu His Arg Leu Lys Arg Leu Arg Lys Arg Leu Lys
1               5                   10                  15

<210> SEQ ID NO 21
<211> LENGTH: 4
<212> TYPE: PRT
<213> ORGANISM: Artificial Sequence
<220> FEATURE:
<223> OTHER INFORMATION: synthesized peptide

<400> SEQUENCE: 21

Leu Lys Arg Leu
1

<210> SEQ ID NO 22
<211> LENGTH: 37
<212> TYPE: PRT
<213> ORGANISM: Homo sapiens

<400> SEQUENCE: 22

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
                35

<210> SEQ ID NO 23
<211> LENGTH: 23
<212> TYPE: PRT
<213> ORGANISM: Xenopus laevis

<400> SEQUENCE: 23

Gly Ile Gly Lys Phe Leu His Ser Ala Lys Lys Phe Gly Lys Ala Phe
1               5                   10                  15

Val Gly Glu Ile Met Asn Ser
                20
```

PEPTIDE WITH ANTI-AGING EFFECT AND USE THEREOF

TECHNICAL FIELD

The present invention relates to a peptide having an anti-aging effect and use thereof. In particular, the present invention relates to an anti-aging agent comprising a peptide having the effect of promoting fibroblast growth, promoting hyaluronic acid production or contracting collagen gels and to use thereof.

BACKGROUND ART

The dermis makes up the bulk of the skin and is mainly composed of fibroblasts and matrix components. Fibroblasts produce proteins such as collagen as well as glycosaminoglycans such as hyaluronic acid to form connective tissue, and are thus play an important role in the skin. The reduction of the fibroblast functions due to aging or other causes may lead to the reduction and degeneration of collagen, hyaluronic acid and other matrix components. Oxidative stress such as ultraviolet light also damages the skin and makes it rough, and causes other adverse effects. Due to the reduction of the matrix components and oxidative stress, aging of the skin occurs, which causes wrinkles, spots, dull appearance, the loss of the smooth texture, the reduction of the elasticity, and other signs of aging.

The functions of collagen and hyaluronic acid have drawn attention as a target for preventing aging of the skin. Conventionally, hyaluronic acid derived from cockscombs or other origins is added to anti-aging agents. However, hyaluronic acid is a high molecular weight molecule, and thus even when hyaluronic acid cosmetics are directly applied to the skin, hyaluronic acid is difficult to be absorbed to the skin. Collagen injections to the skin are also used, but the injected collagen disappears from the skin in a short period of time. Subcutaneous implant therapy using fibroblasts derived from autologous stem cells is also attempted, but the implanted fibroblasts are difficult to remain at the site of implantation.

To address these problems, a search has been actively conducted for natural substances that promote the growth of fibroblasts in the dermis and thereby enhance the production of collagen and hyaluronic acid by the cells. Many natural substances with such an effect have been reported, including various plant-derived substances such as an aqueous chlorella extract, an aloe vera extract, a prickly pear extract, an apricot kernel extract and a passion flower extract.

A peptide of 20 amino acid residues or less is easy to design, and efficient synthetic methods and analysis methods therefor have already been established. Such a peptide thus has the advantage of mass production at low cost. Another advantage is that the peptide is less antigenic and hence when used as an ingredient of a pharmaceutical product, the peptide is less likely to cause adverse side effects. The peptide is very close to practical applications as an ingredient of quasi-drugs or cosmetics. A further advantage is that the peptide contains naturally occurring amino acids and hence is safe with no irritating or sensitizing properties and easily metabolized. There is therefore no obstacle to advancing research and development.

Peptides with various physiological activities, such as the effect of promoting fibroblast growth, are expected to be discovered and developed.

An attempt has been made to improve the skin conditions by applying peptides to the skin. Patent Literature 1, for example, discloses an anti-aging preparation for cutaneous application and an anti-aging cosmetic preparation, the preparations each comprising component (A) a synthetic peptide of 3 to 8 amino acids or a derivative thereof, and component (B) a hydrolyzed collagen with a molecular weight ranging from 500 to 5,000 or a derivative thereof. However, Patent Literature 1 does not disclose an anti-aging preparation for cutaneous application or anti-aging cosmetic preparation comprising a peptide as a single active ingredient.

CITATION LIST

Patent Literature

Patent Literature 1: JP 2011-42613 A

SUMMARY OF INVENTION

Technical Problem

An object of the present invention to discover a short peptide having an anti-aging effect and to provide a novel anti-aging agent comprising the peptide as an active ingredient.

Solution to Problem

The present invention was made to solve the above problems and encompasses the following.
(1) A peptide consisting of an amino acid sequence ELKLIFLHRLKRLRKRLKRK (SEQ ID NO: 1) or a partial sequence thereof and having one or more effects selected from the group consisting of promoting fibroblast growth, promoting hyaluronic acid production and contracting a collagen gel, or a derivative or salt of the peptide.
(2) The peptide or a derivative or salt thereof according to the above (1), wherein the peptide consists of an amino acid sequence KLIFLHRLKRLRKRLK (SEQ ID NO: 20) or a partial sequence thereof.
(3) The peptide or a derivative or salt thereof according to the above (1) or (2), wherein the partial sequence comprises an amino acid sequence selected from the group consisting of KLIFL (SEQ ID NO: 4), IFLHR (SEQ ID NO: 6), LHRLK (SEQ ID NO: 8), HRLKR (SEQ ID NO: 9), RLKRL (SEQ ID NO: 10), LKRLR (SEQ ID NO: 11) and LRKRL (SEQ ID NO: 14).
(4) The peptide or a derivative or salt thereof according to any one of the above (1) to (3), wherein the partial sequence comprises LKR (SEQ ID NO: 19).
(5) The peptide or a derivative or salt thereof according to the above (4), wherein the partial sequence is HRLKR (SEQ ID NO: 9), RLKRL (SEQ ID NO: 10) or LKRLR (SEQ ID NO: 11).
(6) The peptide or a derivative or salt thereof according to any one of the above (1) to (5), having an amidated C-terminus.
(7) The peptide or a derivative or salt thereof according to any one of the above (1) to (6), having an acetylated N-terminus.
(8) An anti-aging agent comprising the peptide or a derivative or salt thereof according to any one of the above (1) to (7) as an active ingredient.
(9) A cosmetic product comprising the anti-aging agent according to the above (8).
(10) A quasi-drug comprising the anti-aging agent according to the above (8).

(11) A pharmaceutical product comprising the anti-aging agent according to the above (8).
(12) A food or drink product comprising the anti-aging agent according to the above (8).
(13) A supplement comprising the anti-aging agent according to the above (8).

Advantageous Effects of Invention

The present invention provides a short peptide having an anti-aging effect and a novel anti-aging agent comprising the peptide as an active ingredient. The anti-aging agent of the present invention has the effects of promoting fibroblast growth, promoting hyaluronic acid synthesis and contracting collagen gels and is thus useful as an ingredient of cosmetics, quasi-drugs, pharmaceutical products, food or drink products and supplements. Since efficient synthetic methods and analysis methods for a short peptide have already been established, the present short peptide of 20 amino acid residues or less serving as an active ingredient has the advantage of mass production at low cost. The short peptide is less antigenic and hence when used as an ingredient of a pharmaceutical product, the short peptide has the advantage of being less likely to cause adverse side effects.

DESCRIPTION OF EMBODIMENTS

Figure 1:
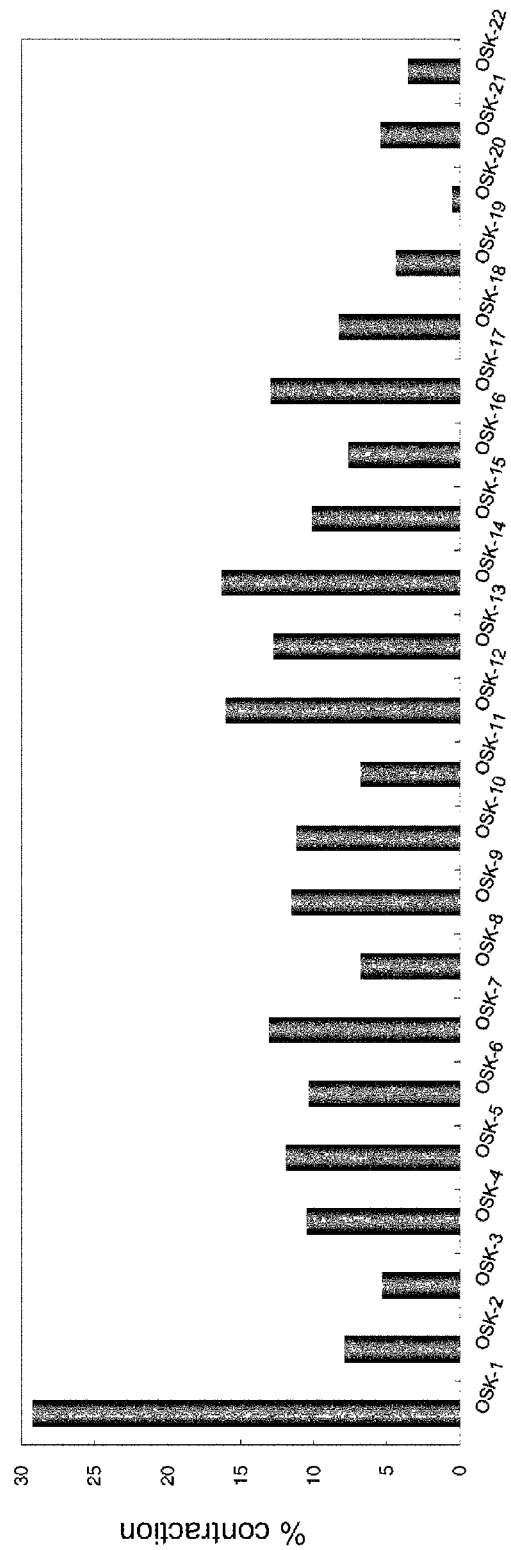
FIG. 1 is a chart showing the effect of contracting collagen gels.

The inventors previously identified a 30-amino acid peptide, AG30, with angiogenic and antimicrobial effects (J. Cell. Mol. Med., 2008; 13: 535-46) and developed a modified version of the peptide that exhibits more potent angiogenic and antimicrobial effects (J. Cell. Mol. Med., Vol. 16, No. 7, 2012, pp. 1629-1639, WO2010/061915, WO2010/101237, WO2010/137594, JP 2012-14583 A). The inventors further investigated the modification of AG30 and discovered a 20-amino acid peptide with an anti-aging effect. The inventors also discovered that a fragment of the peptide also has an anti-aging effect. Thus the inventors completed the present invention.
Peptide
The present invention provides a peptide having one or more effects selected from the group consisting of promoting fibroblast growth, promoting hyaluronic acid production and contracting collagen gels, or a derivative or salt of the peptide (hereinafter, the peptide, the derivative and the salt are collectively also called "the peptide of the present invention"). The peptide of the present invention is of the amino acid sequence ELKLIFLHRLKRLRKRLKRK (SEQ ID NO: 1) or a part of the amino acid sequence of SEQ ID NO: 1, and has one or more effects selected from the group consisting of promoting fibroblast growth, promoting hyaluronic acid production and contracting collagen gels.
Preferably, the partial sequence of the amino acid sequence of SEQ ID NO: 1 consists of 3 or more amino acids, more preferably consists of 4 or more amino acids, and even more preferably consists of 5 or more amino acids.

In particular, the partial sequence preferably consists of any 3 to 19 contiguous amino acids selected from the amino acid sequence of SEQ ID NO: 1, more preferably consists of any 4 to 16 contiguous amino acids selected from the amino acid sequence of SEQ ID NO: 1, even more preferably consists of any 4 to 10 contiguous amino acids selected from the amino acid sequence of SEQ ID NO: 1, and particularly preferably consists of any 5 contiguous amino acids selected from the amino acid sequence of SEQ ID NO: 1.
Preferably, the partial sequence of the amino acid sequence of SEQ ID NO: 1 is a peptide consisting of the amino acid sequence KLIFLHRLKRLRKRLK (SEQ ID NO: 20) or a part of the amino acid sequence of SEQ ID NO: 20 and having one or more effects selected from the group consisting of promoting fibroblast growth, promoting hyaluronic acid production and contracting collagen gels.
Preferably, the partial sequence of the amino acid sequence of SEQ ID NO: 1 or the partial sequence of the amino acid sequence of SEQ ID NO: 20 comprises an amino acid sequence selected from the group consisting of KLIFL (SEQ ID NO: 4), IFLHR (SEQ ID NO: 6), LHRLK (SEQ ID NO: 8), HRLKR (SEQ ID NO: 9), RLKRL (SEQ ID NO: 10), LKRLR (SEQ ID NO: 11) and LRKRL (SEQ ID NO: 14). Preferably, the partial sequence of the amino acid sequence of SEQ ID NO: 1 or the partial sequence of the amino acid sequence of SEQ ID NO: 20 comprises LKR (SEQ ID NO: 19). More preferably, the partial sequence of the amino acid sequence of SEQ ID NO: 1 or the partial sequence of the amino acid sequence of SEQ ID NO: 20 comprises LKR (SEQ ID NO: 19), RLKR (SEQ ID NO: 18), LKRL (SEQ ID NO: 21), HRLKR (SEQ ID NO: 9), RLKRL (SEQ ID NO: 10) or LKRLR (SEQ ID NO: 11).
The peptide of the present invention is particularly preferably a 5-residue peptide consisting of the amino acid sequence HRLKR (SEQ ID NO: 9), RLKRL (SEQ ID NO: 10) or LKRLR (SEQ ID NO: 11).
The peptide derivative of the present invention is derived from the peptide with a particular amino acid sequence and the C-terminus of the peptide derivative may be a carboxyl group (—COOH), a carboxylate (—COO⁻), an amide (—CONH$_2$) or an ester (—COOR). Examples of R of the ester include $C_{1-6}$ alkyl groups such as methyl, ethyl, n-propyl, isopropyl and n-butyl; $C_{3-8}$ cycloalkyl groups such as cyclopentyl and cyclohexyl; $C_{6-12}$ aryl groups such as phenyl and α-naphthyl; $C_{7-14}$ aralkyl groups including phenyl-$C_{1-2}$ alkyl groups, such as benzyl and phenethyl, and α-naphthyl-$C_{1-2}$ alkyl groups, such as α-naphthylmethyl; and a pivaloyloxymethyl group, which is commonly used as an ester for oral administration. Examples of the amide include an amide; an amide substituted with one or two $C_{1-6}$ alkyl groups; an amide substituted with one or two $C_{1-6}$ alkyl groups substituted with a phenyl group; and an amide that forms a 5- to 7-membered azacycloalkane together with the nitrogen atom of the amide group. When the peptide of the present invention has a carboxyl group or a carboxylate at a position other than the C-terminus, the peptide derivative of the present invention also includes those in which the carboxyl group or the carboxylate is amidated or esterified. Preferably, the C-terminus of the peptide derivative of the present invention is amidated.
The peptide derivative of the present invention also includes those in which the N-terminal amino group is protected with a protecting group (for example, a $C_{1-6}$ acyl group including a formyl group and $C_{2-6}$ alkanoyl groups such as acetyl), those in which a N-terminal glutamyl group generated by in vivo cleavage of the N-terminus is converted to a pyroglutamate, and those in which a substituent (for example, —OH, —SH, an amino, imidazole, indole, or guanidino group) on an amino acid side chain in the molecule is protected with a suitable protecting group (for example, a $C_{1-6}$ acyl group including a formyl group and $C_{2-6}$ alkanoyl groups such as acetyl). The peptide derivative of the present invention preferably has an acetylated N-terminus. More preferably, the peptide derivative has an acetylated N-terminus and an amidated C-terminus.

The side chains of the amino acids constituting the peptide derivative of the present invention may be modified with any substituent. Examples of the substituent include, but are not limited to, a fluorine atom, a chlorine atom, a cyano group, a hydroxy group, a nitro group, an alkyl group, a cycloalkyl group, an alkoxy group, an amino group, and a phosphate group. The side-chain substituent may be protected with a protecting group. The derivative of the peptide of the present invention also includes glycopeptides, which are peptides having sugar chains attached thereto.

The peptide of the present invention or a derivative thereof may form a salt. The salt is preferably physiologically acceptable. Examples of the physiologically acceptable salt include salts with acids such as hydrochloric acid, sulfuric acid, phosphoric acid, lactic acid, tartaric acid, maleic acid, fumaric acid, oxalic acid, malic acid, citric acid, oleic acid, palmitic acid, nitric acid, phosphoric acid, trifluoroacetic acid, methanesulfonic acid, benzenesulfonic acid, and p-toluenesulfonic acid; salts with alkali metals or alkaline earth metals such as sodium, potassium, and calcium; salts with aluminum hydroxide or carbonate; and salts with triethylamine, benzylamine, diethanolamine, t-butylamine, dicyclohexylamine, arginine, etc. Among them, more preferred are hydrochloric acid salts, acetic acid salts and trifluoroacetic acid salts.

The peptide of the present invention or a derivative thereof may comprise a non-natural amino acid to the extent that it does not affect the characteristics of the peptide or derivative. The peptide of the present invention or a derivative thereof may comprise another substance linked thereto to the extent that it does not affect the characteristics of the peptide or derivative. Examples of the substance linkable to the peptide include other peptides, lipids, sugars, sugar chains, an acetyl group, and naturally occurring or synthetic polymers. The peptide of the present invention may be subjected to modification such as glycosylation, side-chain oxidation, and phosphorylation to the extent that it does not affect the characteristics of the peptide.

The peptide of the present invention or a derivative or salt thereof can be produced by solid-phase synthesis (the Fmoc or Boc method) or liquid-phase synthesis in accordance with any known standard peptide synthesis protocol. Alternatively, the peptide of the present invention or a derivative or salt thereof can be produced by using a transformant carrying an expression vector containing a DNA encoding the peptide of the present invention. Further alternatively, the peptide of the present invention or a derivative or salt thereof can be produced by preparing a peptide using a transformant carrying an expression vector containing a DNA encoding a peptide comprising the peptide of the present invention, and cleaving the resulting peptide with a suitable protease or peptidase. Further alternatively, the peptide of the present invention or a derivative or salt thereof can be produced by a method using an in vitro transcription-translation system.

The peptide of the present invention has one or more effects selected from the group consisting of promoting fibroblast growth, promoting hyaluronic acid production and contracting collagen gels. Fibroblasts produce proteins such as collagen as well as glycosaminoglycans such as hyaluronic acid to form connective tissue, and are thus play an important role in the skin. The reduction of the fibroblast functions due to aging or other causes may lead to the reduction and degeneration of collagen, hyaluronic acid and other matrix components. Oxidative stress such as ultraviolet light also damages the skin and makes it rough, and causes other adverse effects. Due to the reduction of the matrix components and oxidative stress, aging of the skin occurs, which causes wrinkles, sagging, spots, dull appearance, the loss of the smooth texture, the reduction of the elasticity, and other signs of aging. Hence a peptide with the effect of promoting fibroblast growth or promoting hyaluronic acid production prevents wrinkles and sagging of the skin and is useful for anti-aging. A peptide with the effect of contracting collagen gels prevents the reduction of the skin elasticity and is useful for anti-aging.

The effect of promoting fibroblast growth by the peptide used in the present invention is determined by, for example, the method described in Example 2. The effect of promoting hyaluronic acid production by the peptide used in the present invention is determined by, for example, the method described in Example 4. The effect of contracting collagen gels by the peptide used in the present invention is determined by, for example, the method described in Example 6.

The peptide having the effect of promoting fibroblast growth is preferably a peptide consisting of the amino acid sequence of any of SEQ ID NOs: 1, 3, 4, 6, 8, 9, 10, 11, 12, 14, 15, 16 and 17, and is more preferably a derivative of the peptide having an acetylated N-terminus and an amidated C-terminus.

The peptide having the effect of promoting hyaluronic acid production is preferably a peptide consisting of the amino acid sequence of any of SEQ ID NOs: 1, 2, 4, 6, 8, 9, 10, 11, 14, 15, 16, 18 and 19, and is more preferably a derivative of the peptide having an acetylated N-terminus and an amidated C-terminus.

The peptide having the effect of contracting collagen gels is preferably a peptide consisting of the amino acid sequence of any of SEQ ID NOs: 1 to 19, and is more preferably a derivative of the peptide having an acetylated N-terminus and an amidated C-terminus.

Anti-Aging Agent and Use Thereof

The present invention also provides an anti-aging agent comprising the peptide of the present invention as an active ingredient. The anti-aging agent of the present invention exhibits one or more effects selected from the group consisting of promoting fibroblast growth, promoting hyaluronic acid production and contracting collagen gels, thereby achieving an excellent anti-aging effect. Accordingly, the anti-aging agent of the present invention is also called a fibroblast growth promoter, a hyaluronic acid production promoter or a collagen gel contracting agent. The anti-aging agent of the present invention can be provided in the form of, for example, a cosmetic product, a quasi-drug, a pharmaceutical product, a food or drink product or a supplement.

The present invention also provides a cosmetic product comprising the anti-aging agent of the invention. The cosmetic product of the present invention can be appropriately provided as, for example, a moisturizing cosmetic product, a whitening cosmetic product or an anti-wrinkle cosmetic product.

The present invention also provides a quasi-drug comprising the anti-aging agent of the invention. The quasi-drug of the present invention can be appropriately provided as, for example, a moisturizer, a whitening agent, an anti-wrinkle agent or a preparation for cutaneous application.

The form of the cosmetic product or quasi-drug comprising the anti-aging agent of the present invention is not particularly limited and examples thereof include facial lotions, milky lotions, facial essences, facial packs, makeup base lotions, makeup base creams, makeup foundations (emulsion type, cream type and ointment type), eye colors, cheek colors, lip colors, hand creams, leg creams, body lotions, shampoos, conditioners, hair treatments, hair care agents, hair styling agents, bath additives, body soaps and soaps.

The cosmetic product or quasi-drug comprising the anti-aging agent of the present invention may comprise, in addition to the anti-aging agent of the present invention, other ingredients commonly used in cosmetics or quasi-drugs, as appropriate for the purpose. Examples of said other ingredients include oils, wetting agents, moisturizers, emulsifiers, ultraviolet absorbers, surfactants, antioxidants, stabilizers, solubilizers, thickeners, fillers, sequestrants, sunscreens, defoamers, softeners, colorants, antiseptics, propellants, acidifying and basifying agents, silicones, vitamins, dyes, pigments, nanopigments, fragrances, organic solvents such as alcohols, and water.

The present invention also provides a pharmaceutical product comprising the anti-aging agent of the invention. The pharmaceutical product of the present invention can be appropriately provided as a pharmaceutical product for preventing or treating diseases caused by the reduction in the ability of fibroblasts to proliferate and/or to produce hyaluronic acid. The pharmaceutical product can also be appropriately provided as a pharmaceutical product for treating skin damage (particularly in the dermis) etc. that are alleviated by promoting fibroblast growth and/or hyaluronic acid production.

The pharmaceutical product of the present invention can be produced by formulating the peptide of the present invention or a derivative or salt thereof as an active ingredient together with a pharmaceutically acceptable carrier or additive as appropriate. In particular, the pharmaceutical product can be provided in the form of oral preparations such as tablets, coated tablets, pills, powders, granules, capsules, liquids, suspensions and emulsions; or parenteral preparations such as injections, infusions, suppositories, ointments, patches and liquids. The amount of the carrier or additive to be added can be determined as appropriate based on the range typically used in the pharmaceutical field. The carrier or additive that may be added is not particularly limited and examples thereof include various types of carriers such as water, physiological saline, other aqueous solvents, and aqueous or oily base materials; and various types of additives such as excipients, binders, pH adjusters, disintegrants, absorption promoters, lubricants, colorants, flavors and fragrances.

Examples of the additives that may be added to tablets, capsules, etc. include binders such as gelatin, corn starch, tragacanth, and gum arabic; excipients such as crystalline cellulose; swelling agents such as corn starch, gelatin, and alginic acid; lubricants such as magnesium stearate; sweeteners such as sucrose, lactose, and saccharin; and flavors such as peppermint flavor, wintergreen oil, and cherry flavor. When the unit dosage form is a capsule, a liquid carrier such as oils and fats can be further added in addition to the above types of materials. A sterile composition for injection can be prepared in accordance with a usual pharmaceutical practice (for example, by dissolving or suspending the active ingredient in a solvent such as water for injection or a natural vegetable oil). Aqueous liquids for injection that may be used are, for example, physiological saline and an isotonic solution containing glucose and/or other auxiliary substances (for example, D-sorbitol, D-mannitol, sodium chloride, etc.). The aqueous liquids for injection may be used in combination with an appropriate solubilizer, such as alcohols (e.g., ethanol), polyalcohols (e.g., propylene glycol, polyethylene glycol, etc.), and nonionic surfactants (e.g., polysorbate 80™, HCO-50, etc.). Oily liquids that may be used are, for example, sesame oil and soybean oil. The oily liquids may be used in combination with a solubilizer such as benzyl benzoate and benzyl alcohol. Other additives that may be added are, for example, buffering agents (e.g., a phosphate buffer, a sodium acetate buffer, etc.), soothing agents (e.g., benzalkonium chloride, procaine hydrochloride, etc.), stabilizers (e.g., human serum albumin, polyethylene glycol, etc.), preservatives (e.g., benzyl alcohol, phenol, etc.) and antioxidants.

The preparations produced in the above manner are safe and have low toxicity, and thus can be administered to, for example, humans and other mammals (e.g., rats, mice, rabbits, sheep, pigs, cows, cats, dogs, monkeys, etc.).

The dosage varies with, for example, the subject to which the preparations are to be administered, the target disease, and the route of administration. The dosage for oral administration to a human adult (body weight: 60 kg) is, for example, typically about 0.1 to 100 mg of the active ingredient per day, preferably about 1.0 to 50 mg of the active ingredient per day, and more preferably about 1.0 to 20 mg of the active ingredient per day. The dosage for parenteral administration by intravenous injection to a human adult (body weight: 60 kg) is, for example, typically about 0.01 to 30 mg of the active ingredient per day, preferably about 0.1 to 20 mg of the active ingredient per day, and more preferably about 0.1 to 10 mg of the active ingredient per day. The total daily dosage may be given as a single dose or several divided doses.

The present invention also provides a food or drink product comprising the anti-aging agent of the invention. The food or drink product of the present invention can be appropriately provided as a food or drink product for promoting fibroblast growth, promoting hyaluronic acid production or contracting collagen gels. The food or drink product includes health foods, functional foods, foods for specified health use, and foods for sick people. The form of the food or drink product is not particularly limited and examples thereof include drinks such as tea drink, refreshing drink, carbonated drink, nutritional drink, fruit juice, and lactic drink; noodles such as buckwheat noodle, wheat noodle, Chinese noodle, and instant noodle; sweets and bakery products such as drop, candy, gum, chocolate, snack, biscuit, jelly, jam, cream, pastry, and bread; fishery and livestock products such as fish sausage, ham, and sausage; dairy products such as processed milk and fermented milk; fats, oils, and processed foods thereof, such as vegetable oil, oil for deep frying, margarine, mayonnaise, shortening, whipped cream, and dressing; seasonings such as sauce and dipping sauce; retort pouch foods such as curry, stew, rice-bowl cuisine, porridge, and rice soup; and frozen desserts such as ice cream, sherbet, and shaved ice.

The present invention also provides a supplement comprising the peptide etc. of the present invention. The supplement of the present invention is suitable as a supplement for promoting osteogenesis or as a supplement for preventing or alleviating cartilage or joint disorders. The supplement can be provided in the form of, for example, tablets, granules, powders or drinks.

The supplement comprising the anti-aging agent of the present invention may be provided in any dosage form produced by formulating the active ingredient together with any types of auxiliary agents, including, for example, sugars such as dextrin and starch; proteins such as gelatin, soybean protein, and corn protein; amino acids such as alanine, glutamine, and isoleucine; polysaccharides such as cellulose and gum arabic; and oils and fats such as soybean oil and medium-chain triglycerides.

The present invention further includes the following.
(a) Use of the peptide of the present invention or a derivative or salt thereof for production of an anti-aging agent.
(b) The peptide of the present invention or a derivative or salt thereof for promoting fibroblast growth, promoting hyaluronic acid production or contracting a collagen gel.
(c) A non-therapeutic method for anti-aging, the method comprising administering an effective amount of the peptide of the present invention or a derivative or salt thereof to a mammal.
(d) An anti-aging method comprising administering an effective amount of the peptide of the present invention or a derivative or salt thereof to a mammal.
(e) A method for treating skin damage, the method comprising administering an effective amount of the peptide of the present invention or a derivative or salt thereof to a mammal.

EXAMPLES

The present invention will be described below in detail with reference to Examples, but the present invention is not limited thereto.

Example 1: Synthesis of Peptides

Protected peptide resins were synthesized by the Fmoc method using a fully automated solid-phase synthesizer in accordance with the methods described in the following publications: Solid Phase Peptide Synthesis, Pierce (1984); Fmoc solid synthesis: a practical approach, Oxford University Press (2000); The Fifth Series of Experimental Chemistry (Jikken Kagaku Koza), vol. 16, Yukikagobutsu no Gosei IV; etc. To the protected peptide resins were added trifluoroacetic acid (TFA) and a scavenger (a mixture of thioanisole, ethanedithiol, phenol, triisopropylsilane, water, etc.) to cleave the peptides from the resin and deprotect the side chains. The resulting crude peptides were purified by eluting from a reversed-phase HPLC column (ODS) with a gradient system of 0.10 TFA-$H_2O$/$CH_3CN$. The fractions containing the peptides of interest were collected and freeze-dried. The amino acid sequences of the synthesized peptides were determined using an amino acid sequencer, G1000A (Hewlett-Packard), PPSQ-23A (Shimadzu Corporation), or Procise LC (ABI). The sequences of the synthesized peptides are shown below. In Table 1, the peptides indicated with asterisks (*) were subjected to N-terminal acetylation and C-terminal amidation.

Figure 4:
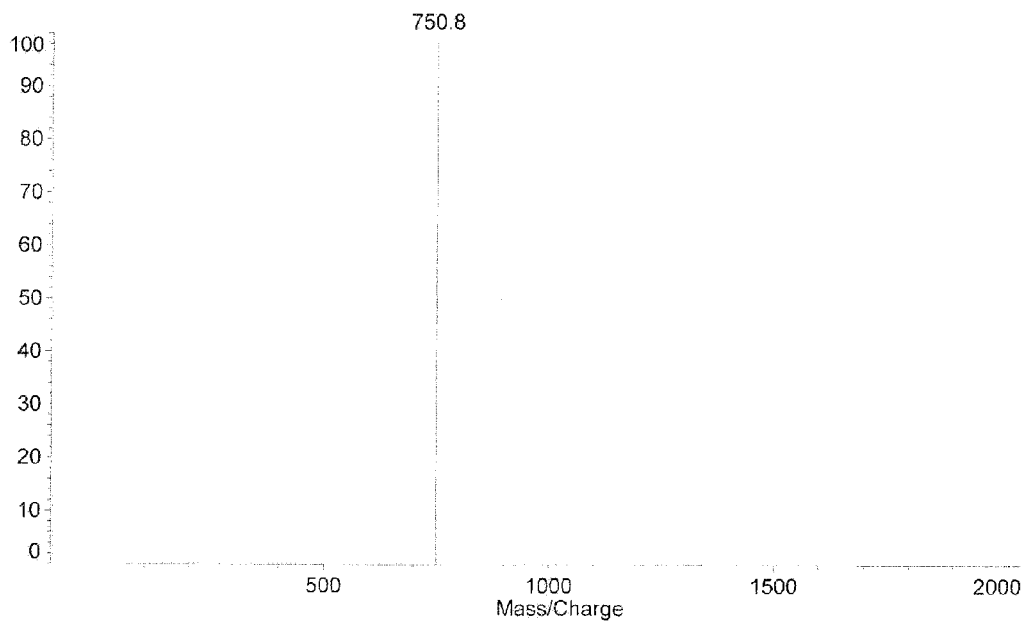
FIG. 4 is a chart of a peptide (OSK-9) consisting of the amino acid sequence of SEQ ID NO: 9.

The molecular weight of the synthesized OSK-9 (see Table 1) was determined by MALDI-TOF mass analysis using Axima CFR (Shimadzu Corporation). The MALDI-TOF/MS spectrum is shown in FIG. 4.

TABLE 1

| Peptide | Amino acid sequence | SEQ ID NO |
|---|---|---|
| OSK-1 (*) | ELKLIFLHRL KRLRKRLKRK | SEQ ID NO: 1 |
| OSK-2 (*) | ELKLI | SEQ ID NO: 2 |
| OSK-3 (*) | LKLIF | SEQ ID NO: 3 |
| OSK-4 (*) | KLIFL | SEQ ID NO: 4 |
| OSK-5 (*) | LIFLH | SEQ ID NO: 5 |
| OSK-6 (*) | IFLHR | SEQ ID NO: 6 |
| OSK-7 (*) | FLHRL | SEQ ID NO: 7 |
| OSK-8 (*) | LHRLK | SEQ ID NO: 8 |
| OSK-9 (*) | HRLKR | SEQ ID NO: 9 |
| OSK-10 (*) | RLKRL | SEQ ID NO: 10 |
| OSK-11 (*) | LKRLR | SEQ ID NO: 11 |
| OSK-12 (*) | KRLRK | SEQ ID NO: 12 |
| OSK-13 (*) | RLRKR | SEQ ID NO: 13 |
| OSK-14 (*) | LRKRL | SEQ ID NO: 14 |
| OSK-15 (*) | RKRLK | SEQ ID NO: 15 |
| OSK-16 (*) | KRLKR | SEQ ID NO: 16 |
| OSK-17 (*) | RLKRK | SEQ ID NO: 17 |
| OSK-18 (*) | RLKR | SEQ ID NO: 18 |
| OSK-19 (*) | LKR | SEQ ID NO: 19 |
| OSK-20 | HRLKR | SEQ ID NO: 9 |
| OSK-21 | RLKRL | SEQ ID NO: 10 |
| OSK-22 | RLKR | SEQ ID NO: 18 |
| OSK-23 | LKR | SEQ ID NO: 19 |

Example 2: Study of the Effect of Promoting Fibroblast Growth (1)

The effects of the peptides on fibroblast growth were examined.
(1) Experimental Method
The fibroblast growth-promoting activity of the peptides was determined using Cell Counting Kit (WST-1) (Dojindo Laboratories). As a control, a group containing no peptide was used. Normal human dermal fibroblasts (from newborns) (Kurabo Industries Ltd., hereinafter called NHDF) were seeded in 96-well plates ($0.5 \times 10^4$ cells/100 μL per well). The culture medium used was Medium 106 (containing 1% FBS without growth supplements). About 3 hours after cell seeding, 100 μL of a solution of each peptide in the culture medium was added to a final peptide concentration of 0.3, 1, 3, 10, or 30 μM. To control wells, 100 μL of the culture medium alone was added. To blank wells containing no cells, 200 μL of the culture medium alone was added. The cells were cultured in a $CO_2$ incubator for 2 days. After the culture, 20 μL of the WST-1 reagent was added to each well and the plates were allowed to stand in a $CO_2$ incubator for about 2 to 4 hours. The absorbance at 450 nm and 620 nm was determined with a microplate reader (Wallac 1420 ARVOsx (program: WST-1)), and the measured values were corrected by the equation: OD450-OD620. The net OD450 was calculated by subtracting the mean OD450-OD620 of the blank wells from the OD450-OD620 of the test wells. The percent fibroblast growth was calculated as the ratio (%) of the net OD450 of each peptide addition group to that of the control group. The effect of promoting fibroblast growth was evaluated on the basis of the percent fibroblast growth.

(2) Results

The highest value of the percent fibroblast growth over the concentrations tested (0.3, 1, 3, 10, and 30 μM) was determined for OSK-1 to OSK-17 and the results are shown in Table 2. The assay confirmed that OSK-1, OSK-3, OSK-4, OSK-6, OSK-9, OSK-10, OSK-11, OSK-12, OSK-14, OSK-15, OSK-16 and OSK-17 exhibited the effect of promoting fibroblast growth at concentrations of 0.3 to 30 μM.

TABLE 2

| Peptide | Fibroblast growth (% of control) |
|---|---|
| OSK-1 | 146.4 |
| OSK-2 | 99.7 |
| OSK-3 | 104.7 |
| OSK-4 | 102.6 |
| OSK-5 | 97.6 |
| OSK-6 | 111.8 |
| OSK-7 | 96.8 |
| OSK-8 | 98.8 |
| OSK-9 | 122.8 |
| OSK-10 | 116.2 |
| OSK-11 | 112.5 |
| OSK-12 | 100.3 |
| OSK-13 | 99.3 |
| OSK-14 | 106.8 |
| OSK-15 | 102.9 |
| OSK-16 | 106.1 |
| OSK-17 | 104.2 |

Example 3: Study of the Effect of Promoting Fibroblast Growth (2)

The fibroblast growth-promoting activity of OSK-1, OSK-9, OSK-10 and OSK-11, which exhibited higher fibroblast growth-promoting activity in Example 2, were further examined.

(1) Experimental Method

The examination was conducted in the same manner as in Example 2 except that the concentration of each peptide was set at 3, 10, 30, 100 or 300 μM.

(2) Results

The highest value of the percent fibroblast growth over the concentrations tested (3, 10, 30, 100 and 300 μM) was determined for OSK-1, OSK-9, OSK-10 and OSK-11 and the results are shown in Table 3. The assay confirmed that the peptides exhibited the effect of promoting fibroblast growth at concentrations of 30 to 300 μM.

TABLE 3

| Peptide | Fibroblast growth (% of control) |
|---|---|
| OSK-1 | 144.9 |
| OSK-9 | 168.7 |
| OSK-10 | 149.9 |
| OSK-11 | 158.5 |

Example 4: Study of the Effect of Promoting Hyaluronic Acid Production (1)

The effects of the addition of the peptides on the amount of the hyaluronic acid production by fibroblasts were examined.

(1) Experimental Method

The amount of the hyaluronic acid production by fibroblasts was determined by ELISA. As a control, a group containing no peptide was used. NHDF (NB) cells were seeded in 24-well plates and cultured overnight ($2 \times 10^4$ cells/500 μL per well). The culture medium used was Medium 106 (containing 1% FBS without growth supplements). Twenty hours after cell seeding, 500 μL of a solution of each peptide in the culture medium was added to each well to a final peptide concentration of 3, 10, 30, 100 or 300 μM. To control wells, 500 μL of the culture medium alone was added. The cells were cultured in a 5% $CO_2$ incubator at 37° C. for 5 days. After the culture, the culture supernatant was transferred into a 1.5-mL tube and centrifuged at 15,000 rpm at 4° C. for 5 minutes, and the supernatant was harvested in a fresh tube. The amount of hyaluronic acid in the culture supernatant was determined using QnE Hyaluronic Acid (HA) ELISA Assay (Biotech Trading Partners) in accordance with the kit protocol. The percent hyaluronic acid production was calculated as the ratio (%) of the ELISA absorbance of each peptide addition group to that of the control group. The effect of promoting hyaluronic acid production was evaluated on the basis of the percent hyaluronic acid production.

(2) Results

The highest value of the percent hyaluronic acid production over the concentrations tested (3, 10, 30, 100 and 300 μM) was determined for OSK-2 to OSK-17 and the results are shown in Table 4. The assay confirmed that OSK-2, OSK-4, OSK-6, OSK-8, OSK-9, OSK-10, OSK-11, OSK-14, OSK-15 and OSK-16 increased the amount of the hyaluronic acid production by fibroblasts.

TABLE 4

| Peptide | Hyaluronic acid production (% of control) |
|---|---|
| OSK-2 | 184.0 |
| OSK-3 | 79.9 |
| OSK-4 | 212.4 |
| OSK-5 | 65.6 |
| OSK-6 | 160.7 |
| OSK-7 | 75.2 |

TABLE 4-continued

| Peptide | Hyaluronic acid production (% of control) |
|---|---|
| OSK-8 | 110.5 |
| OSK-9 | 182.8 |
| OSK-10 | 198.2 |
| OSK-11 | 112.1 |
| OSK-12 | 72.0 |
| OSK-13 | 74.3 |
| OSK-14 | 123.6 |
| OSK-15 | 103.9 |
| OSK-16 | 110.6 |
| OSK-17 | 81.8 |

Example 5: Study of the Effect of Promoting Hyaluronic Acid Production (2)

(1) Experimental Method

The examination was conducted in the same manner as in Example 4 except that the percent hyaluronic acid production was determined as follows: the amount of hyaluronic acid was quantified from the ELISA calibration curve and the quantified value was used to calculate the ratio (%) of the amount of the hyaluronic acid production of each peptide addition group to that of the control group.

(2) Results

The highest value of the percent hyaluronic acid production over the concentrations tested (3, 10, 30, 100 and 300 µM) was determined for OSK-1, OSK-9 to OSK-11, OSK-18 to OSK-22, and OSK-23 and the results are shown in Table 5. The assay confirmed that OSK-1, OSK-9, OSK-10, OSK-11, OSK-18, OSK-19, OSK-21, OSK-22 and OSK-23 increased the amount of the hyaluronic acid production by fibroblasts.

TABLE 5

| Peptide | Hyaluronic acid production (% of control) |
|---|---|
| OSK-1 | 2715.8 |
| OSK-9 | 540.6 |
| OSK-10 | 409.1 |
| OSK-11 | 255.0 |
| OSK-18 | 131.9 |
| OSK-19 | 117.6 |
| OSK-20 | 94.0 |
| OSK-21 | 109.3 |
| OSK-22 | 101.1 |
| OSK-23 | 113.7 |

Example 6: Study of the Effect of Contracting Collagen Gels (1) Coating of Plates A 30% albumin solution (Sigma) was diluted in DPBS to prepare a 2% albumin solution. To each well of 24-well plates, 1 mL of the solution was dispensed and allowed to stand at room temperature or 37° C. for several hours. Immediately before use of the plates, the 2% albumin solution was removed by aspiration, and the wells were washed twice with DPBS. Then, 0.5 mL of DPBS was added to each well and subsequently removed by aspiration immediately before the addition of a collagen solution.

(2) Preparation of Fibroblast Suspension

Subcultured NHDF cells were treated with trypsin/EDTA, detached from the plate and harvested by centrifugation at 1,200 rpm at room temperature for 3 minutes. The harvested NHDF cells were resuspended in DMEM (containing 2% FBS, Invitrogen) to a density of $2\times10^6$ cells/mL. The cell suspension was placed on ice until use.

(3) Preparation of Collagen Gels

A collagen solution with the formula shown in Table 6 was quickly prepared on ice in an amount greater than that sufficient for the number of wells in use. The prepared collagen solution was mixed with the fibroblast suspension prepared in the above (2) at a ratio of 4:1. The mixture was gently mixed by pipetting. The mixed solution was then gently mixed and warmed in a water bath set at 37° C. so as not to form bubbles. From the 24-well plates coated with the albumin in the above (1), the DPBS was removed and 500 µL of the mixture of the collagen solution and the fibroblast suspension was gently added to each well. The plates were allowed to stand in a 5% $CO_2$ incubator at 37° C. for about 1 hour to allow the polymerization of the collagen.

TABLE 6

| Reagent | Volume per well (µL) |
|---|---|
| Collagen solution, 3 mg/mL, Ultrapure bovine (Sigma) | 250 |
| 10 × DMEM (Sigma) | 31.3 |
| 0.25N NaOH (Sigma) | 12.5 |
| L-glutamine 200 mM (Invitrogen) | 3.1 |
| NaHCO$_3$ solution (7.5% w/v) (Invitrogen) | 15.6 |
| DMEM (Invitrogen) | 87.5 |
| Total | 400 |

(4) Addition of Peptides

To each well containing the polymerized collagen gel, 500 µL of a solution of each peptide in the culture medium was added to a final peptide concentration of 3, 10, 30, 100 or 300 µM. As a control, a group containing no peptide was used. The plates were gently shaken to allow the collagen gels to float in the medium.

(5) Measurement of Collagen Gels

The gels were photographed with a digital camera (COOLPIX 4500, Nikon), and the area of the gels was calculated using an image analysis software (ImageJ 1.43S). The gel area of the control was regarded as 100% and the relative percent area of the gel of each peptide addition group was calculated.

(6) Results

The highest value of the percent contraction over the concentrations tested (3, 10, 30, 100 and 300 µM) was determined for OSK-1 to OSK-22 and the results are shown in FIG. 1. The assay confirmed that OSK-1 to OSK-22 exhibited the effect of contracting collagen gels.

Example 7: Sensitization Test

A sensitization test was performed for OSK-6 and OSK-9 by the h-CLAT assay. As controls, LL-37, magainin, and Peptide-1 were used. LL-37 is a peptide belonging to the cathelicidin family of antimicrobial peptides of mammals and has a high antimicrobial activity. LL-37 is produced by neutrophils, mast cells, epithelial cells, etc. and plays an important role in the defense mechanism against local and systemic infection. LL-37 consists of 37 amino acids (LL-GDFFRKSKEKIGKEFKRIVQRIKDFLRNLVPRTES (SEQ ID NO: 22)). Magainin is an antimicrobial peptide isolated from the skin of frogs and consists of 23 amino acids (GIGKFLHSAKKFGKAFVGEIMNS (SEQ ID NO: 23)). Peptide-1 is a peptide consisting of 19 amino acids and its function is unknown.

(1) Experimental Method

Into a 75-cm² flask was placed 50 mL of a suspension of the human monocytic cell line THP-1 (JCRB accession number: JCRB0112) at a density of $2.0 \times 10^5$ cells/mL in RPMI 1640 culture medium containing 10% FBS and 0.05 mM mercaptoethanol. The cells were precultured for 48 hours. The precultured THP-1 cells were harvested by centrifugation and suspended at $2.0 \times 10^6$ cells/mL in RPMI 1640 culture medium containing 10% FBS and 0.05 mM mercaptoethanol. To each well of 24-well plates, 500 μL of the cell suspension was seeded. To each well containing the seeded cell suspension, 500 μL of each peptide in the same culture medium was added. After 24 hours of incubation, the cells were harvested by centrifugation and were washed twice with PBS containing 0.1% BSA (FACS buffer). The cells were then suspended in 600 μL of FACS buffer containing a 0.01% human γ-globulin solution (Sigma, G2388) and incubated at 4° C. for 10 minutes to block the Fc receptor. The cell suspension was then split into three 180-μL aliquots for conducting an antibody reaction. The aliquots were each transferred to a 1.5-mL tube and centrifuged to give a pellet. To each pellet was added 50 μL of each of solutions of three different FITC-conjugated antibodies, i.e., FITC-conjugated CD86 antibody (Pharmingen; Cat #555657), FITC-conjugated CD54 antibody (Dako; Cat #F7143) and FITC-conjugated isotype control (Mouse IgG) antibody (Dako; Cat #X0927), that were adjusted to an appropriate concentration with FACS buffer. The mixture was incubated at 4° C. for 30 minutes. After the incubation, the cells were harvested by centrifugation and washed twice with FACS buffer. The cells were harvested by centrifugation and suspended in 200 μL of FACS buffer containing 0.625 μg/mL propidium iodide. Then, $1 \times 10^4$ living cells were analyzed by flow cytometry to determine the expression levels of the cell surface antigens. No gating on forward or side scatter was used. The relative fluorescence intensities (RFIs) were calculated from the mean of the measured fluorescence intensities (MFIs) in accordance with the following equation.

$$RFI\,(\%) = \frac{MFI \text{ of test substance-treated cells} - MFI \text{ of test substance-treated isotype control cells}}{MFI \text{ of vehicle-treated cells} - MFI \text{ of vehicle-treated isotype control cells}} \times 100$$

(MFI = Geometric mean fluorescence intensity)

The assay was regarded as successful when the control cells not treated with the test sample (cells treated with the vehicle alone) showed a survival rate of 90% or more. When the survival rate of less than 50% was observed at a particular sample concentration tested, the results for CD86 or CD54 expression at the concentration was excluded from the evaluation. From the survival rates and the RFI values of CD86 and CD54 expressions, the sensitization potentials were evaluated. The sensitization potentials of the test samples were determined to be positive when the RFIs of the antigen expressions in the sample treatment groups satisfy the following equations: the RFI of CD86>150, and the RFI of CD54>200.

(2) Results

Figure 2:
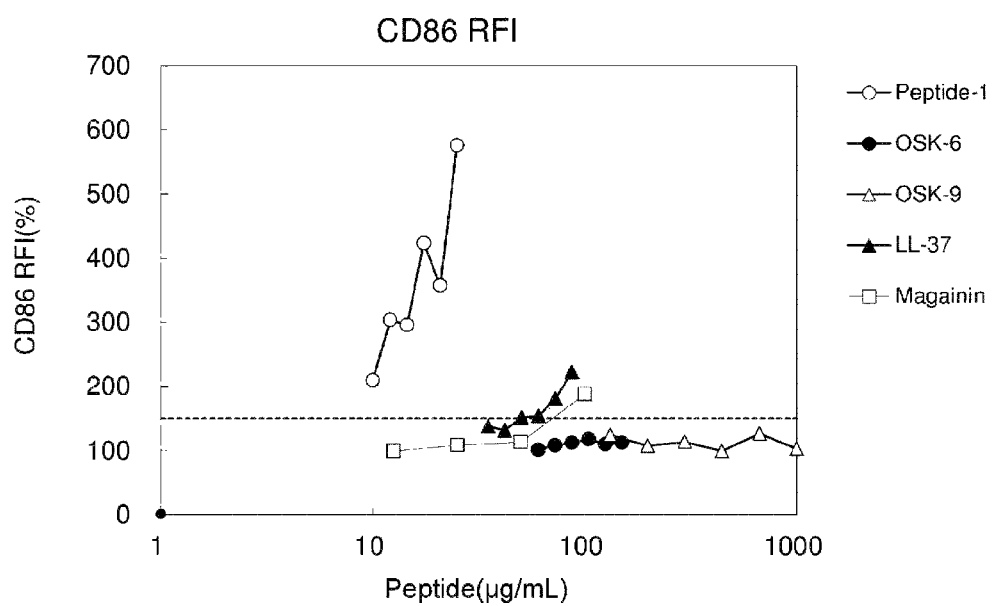
FIG. 2 is a chart showing the expression level of CD86 determined in a sensitization test by the h-CLAT assay.
Figure 3:
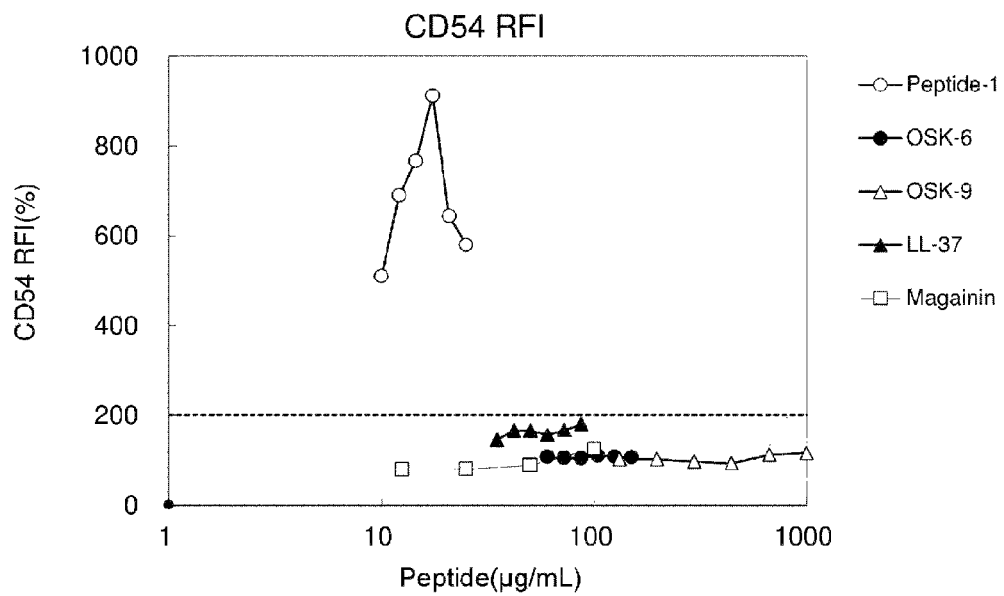
FIG. 3 is a chart showing the expression level of CD54 determined in a sensitization test by the h-CLAT assay.

FIGS. 2 and 3 show the results for CD86 and CD54 expressions, respectively. OSK-6 and OSK-9 are a peptide consisting of 5 amino acids. The sensitization potentials of the peptides yielded negative results even when they were added at high concentrations, indicating that the peptides are highly safe. Peptide-1 showed a strong sensitization potential even at low concentrations. LL-37 and magainin are longer peptides than Peptide-1. For CD54 expression, the sensitization potentials of LL-37 and magainin were negative (FIG. 3), whereas for CD86 expression, the sensitization potentials of the peptides were negative at low concentrations but positive at high concentrations (FIG. 2). The assay results indicated that an increase in the sensitization potential of a peptide is not simply caused by an increase in the number of amino acids and that the sensitization potential of a peptide greatly varies with the sequence.

The present invention is not limited to the embodiments and the examples described above and various modifications are possible within the scope of the claims. Embodiments obtained by appropriately combining the technical means disclosed in the different embodiments are also included in the technical scope of the present invention. All scientific and patent literature cited herein are each incorporated herein by reference in its entirety.

INDUSTRIAL APPLICABILITY

The anti-aging agent of the present invention exhibits the effect of promoting fibroblast growth, promoting hyaluronic acid production or contracting collagen gels, thereby preventing wrinkles or sagging of the skin or the reduction of the skin elasticity. The anti-aging agent is therefore suitable as an ingredient of anti-aging cosmetics, quasi-drugs, pharmaceutical products, food or drink products or supplements.

The invention claimed is:

1. A peptide consisting of the amino acid sequence ELKLIFLHRLKRLRKRLKRK (SEQ ID NO: 1), or a derivative or salt of the peptide, wherein the derivative has a modification selected from C-terminal amidation or esterification, protection of an N-terminal amino group with a protecting group, protection of a substituent on an amino acid side chain in the molecule with a protecting group, a combination of C-terminal amidation or esterification and protection of an N-terminal amino group with a protecting group, a combination of C-terminal amidation or esterification and protection of a substituent on an amino acid side chain in the molecule with a protecting group, a combination of protection of an N-terminal amino group with a protecting group and protection of a substituent on an amino acid side chain in the molecule with a protecting group, and a combination of C-terminal amidation or esterification, protection of an N-terminal amino group with a protecting group and protection of a substituent on an amino acid side chain in the molecule with a protecting group.

2. The peptide or a derivative or salt thereof according to claim 1, wherein the derivative has an amidated C-terminus.

3. The peptide or a derivative or salt thereof according to claim 1, wherein the derivative has an acetylated N-terminus.

4. A preparation for cutaneous application comprising the peptide or a derivative or salt thereof according to claim 1 as an active ingredient.

5. The peptide or a derivative or salt thereof according to claim 1, wherein the derivative has an amidated C-terminus and an acetylated N-terminus.

6. A cosmetic product, a food or drink product or a supplement, each comprising the peptide or a derivative or salt thereof according to claim 1.

7. A composition comprising (a) the peptide or a derivative or salt thereof according to claim 1 and (b) a pharmaceutically acceptable carrier or additive.

8. A peptide consisting of the amino acid sequence ELKLIFLHRLKRLRKRLKRK (SEQ ID NO: 1).

9. A preparation for cutaneous application comprising the peptide of claim 8 as an active ingredient.

10. A cosmetic product, a food or drink product, or a supplement, each comprising the peptide of claim 8.

11. A composition comprising (a) the peptide of claim 8 and (b) a pharmaceutically acceptable carrier or additive.

12. A peptide consisting of the amino acid sequence ELKLIFLHRLKRLRKRLKRK (SEQ ID NO: 1) with an amidated C-terminus.

13. A preparation for cutaneous application comprising the peptide of claim 12 as an active ingredient.

14. A cosmetic product, a food or drink product, or a supplement, each comprising the peptide of claim 12.

15. A composition comprising (a) the peptide of claim 12 and (b) a pharmaceutically acceptable carrier or additive.

16. A peptide consisting of the amino acid sequence ELKLIFLHRLKRLRKRLKRK (SEQ ID NO: 1) with an acetylated N-terminus.

17. A preparation for cutaneous application comprising the peptide of claim 16 as an active ingredient.

18. A cosmetic product, a food or drink product, or a supplement, each comprising the peptide of claim 17.

19. A composition comprising (a) the peptide of claim 16 and (b) a pharmaceutically acceptable carrier or additive.

20. A peptide consisting of the amino acid sequence ELKLIFLHRLKRLRKRLKRK (SEQ ID NO: 1) with an amidated C-terminus and an acetylated N-terminus.

21. A preparation for cutaneous application comprising the peptide of claim 20 as an active ingredient.

22. A cosmetic product, a food or drink product, or a supplement, each comprising the peptide of claim 20.

23. A composition comprising (a) the peptide of claim 20 and (b) a pharmaceutically acceptable carrier or additive.

* * * * *